US00PP30806P2

(12) United States Plant Patent
Horvath

(10) Patent No.: US PP30,806 P2
(45) Date of Patent: Aug. 13, 2019

(54) ***DELOSPERMA* PLANT NAMED 'ORANGE CRUSH'**

(50) Latin Name: ***Delosperma* spp.**
Varietal Denomination: Orange Crush

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 15/732,548

(22) Filed: Nov. 28, 2017

(51) Int. Cl.
*A01H 5/02* (2018.01)

(52) U.S. Cl.
USPC ..... Plt./422

(58) Field of Classification Search
USPC ..... Plt./422
CPC ..... A01H 5/02; A01H 5/00; A01H 6/00
See application file for complete search history.

(56) References Cited

PUBLICATIONS

Greenhouse Management Supplement 2018 New perennial Varieties, retrieved on Oct. 31, 2018, retrieved from the Internet at http://giecdn.blob.core.windows.net/fileuploads/document/2018/05/31/fordigitaledition.pdf, pp. 1 and 14. (Year: 2018).*
Intrinsic Introduction. IPG Tentative New 2017, retrieved on Oct. 31, 2017, retrieved from the Internet at http://intrinsicintroductions.com/wp-content/uploads/New-2017-Plant-List-Tentative.pdf, one page. (Year: 2017).*

* cited by examiner

*Primary Examiner* — June Hwu

(57) ABSTRACT

A new, distinct *Delosperma* plant as illustrated and described, characterized by orange and pink flowers.

1 Drawing Sheet

Figure 1:
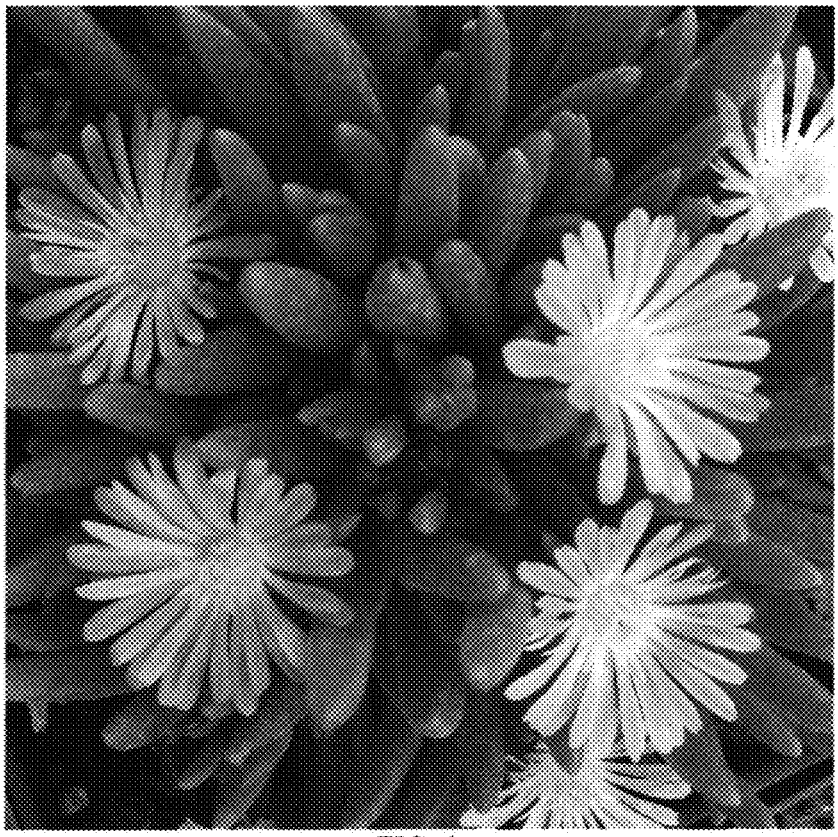

Latin name: *Delosperma* spp.
Cultivar name: 'Orange Crush'.

BACKGROUND OF THE INVENTION

The present invention relates to a new and distinct sport of *Delosperma* plant named 'Orange Crush' characterized by orange and pink flowers, compared to the red and orange of the parent plant. The new *Delosperma* was found at a nursery in a container as a naturally occurring, whole plant sport of *Delosperma* 'P001S', not patented, in Hebron, Ill. in 2013. The selection of the new plant was due to its' orange and pink flowers, compared to the red and orange of the parent plant. Initial asexual reproduction has taken place at a nursery in Hebron, Ill. since 2014 by means of division, and vegetative cuttings. The new *Delosperma* has shown to be stable and identical in reproduction after rooting over 1000 plants from 2014 to 2016. No plants of the new *Delosperma* have been sold in this country, or anywhere in the world, prior to the filing of this application, nor has any disclosure of the new plant been made prior to the filing of this application with the exception of that which was disclosed within one year of filing of this application and was either derived directly or indirectly for the inventor.

SUMMARY OF THE INVENTION

The new *Delosperma* plant named 'Orange Crush' characterized by orange and pink flowers, compared to the red and orange of the parent plant, have been observed to be unique and stable.

Plants of the new *Delosperma* 'Orange Crush' can be compared to plants of *Delosperma* 'P001S', not patented. 1.

The new *Delosperma* plant has orange and pink flowers, compared to the red and orange of the parent plant.

Plants of the new *Delosperma* can be compared to plants of *Delosperma* 'Jewel of Desert Topaz' patented, U.S. Plant Pat. No. 23,492. 1. The new *Delosperma* plant has green foliage RHS color 146 B and C while *Delosperma* 'Jewel of Desert Topaz' plant has a foliage color 143 B and C. 2. The new *Delosperma* plant has flower colors RHS color 23 A in the center and 23 B edge of the petal and 38 C at the base of the petal while *Delosperma* 'Jewel of Desert Topaz' plant has flower colors in a blend of 26 A and 14 A, base 75 B to 75 C blending with 155 A, and apex flushed with 178 B.

DESCRIPTION OF PHOTOGRAPHS

Figure 2:
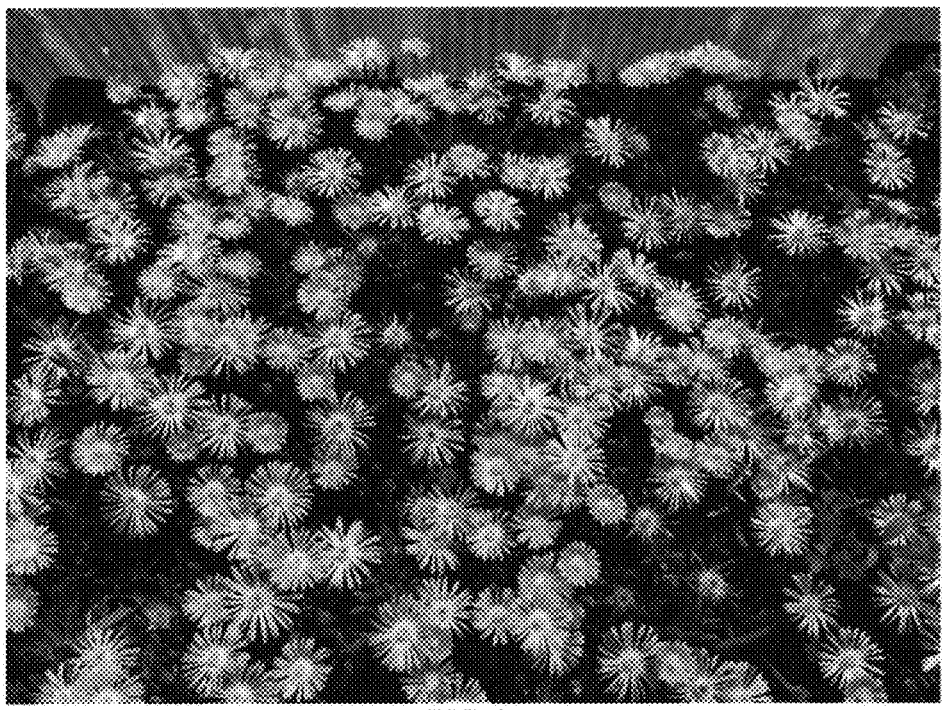

Plants pictured in the drawing were grown for one year.
FIG. 1. Close up of the foliage and flower.
FIG. 2. A picture of many plants blooming together.

DETAILED BOTANICAL DESCRIPTION

In the following description, color references are made to The Royal Horticultural Society Colour Chart (2001). Plants used for the description were grown for one year. Measurements and numerical values represent averages of typical plants.

Botanical classification: *Delosperma* cultivar Orange Crush.
Parentage: A whole plant sport of *Delosperma* 'P001S'.
Propagation: Vegetative division and cutting propagation.
Plant description: Overall habit of the new *Delosperma* is basal clumps, with stems topped by orange and pink flowers May through June.

*Plant height*.—Average 3 cm.
*Plant width*.—25 cm.

*Growth habit*.—Moderately vigorous.
*Stem color*.—165 A in spring, summer, and fall.
*Stem shape*.—Both typical and observed — round.
*Stem texture*.—Glabrous, slightly glossy.
*Stem length*.—3 cm, Stem diameter — 3 mm.
*Internode length*.—10 mm.
*Roots*.—Fibrous.

Foliage:
*Type*.—Succulent.
*Leaf division*.—Simple.
*Leaf attachment*.—Sessile.
*Shape*.—Linear.
*Petiole*.—None.
*Length*.—17 mm.
*Width*.—4 mm.
*Thickness*.—3 mm.
*Margin*.—Entire.
*Leaf apex, typical and observed*.—Acute.
*Leaf bases, typical and observed*.—Cuneate.
*Texture*.—Rounded.
*Leaf arrangement*.—Alternate, crowded.
*Leaf venation pattern*.—None.
*Leaf vein color*.—None.
*Adaxial leaf description*.—Color is 146 B at the tip; 146 C below the tip.
*Abaxial leaf description*.—Color is 146 B at the tip; 146 C below the tip.
*Fall foliage color*.—None noticed.

Flower:
*Aspect*.—Outward to upright.
*Inflorescence type*.—Single on basal flowering stems.
*Inflorescence size*.—27 mm across, 13 mm tall.
*Flower number*.—1 per stem, 10 per plant.
*Flower longevity*.—A few days.
*Bloom period and duration*.—May to June; sporadically to November.
*Blooming habit*.—Solitary on up to 3 cm stems.
*Petal count*.—30, Petal arrangement — rotate, Petal shape — lanceolate.
*Adaxial petal color*.—23 A in center of petal, 23 B on edge of petal with 38 C pink at base.
*Abaxial petal color*.—16 A; 38 B at base.
*Petal apex shape*.—Obtuse.
*Petal bases, typical and observed*.—Acute, 1 mm wide.
*Petal length*.—13 mm, Petal width — 2 mm.
*Petal margin, typical and observed*.—Entire.
*Petaloid*.—Rotate near vertical and placed around stamens, average of 30, lanceolate in shape, margin entire, apex obtuse, base truncate, upper and lower surface smooth, average of 4 mm in length and 1 mm in width, color upper and lower mature and immature surface; 62D blended with 155A, non-fading.
*Bud shape, typical and observed*.—Elliptical.
*Bud length, typical and observed*.—7 mm.
*Bud diameter, typical and observed*.—6 mm.
*Bud color, typical and observed*.—146 C.
*Sepal size*.—2 mm across, 6 mm tall, Sepal number — 5.
*Sepal shape, typical and observed*.—Lanceolate.
*Sepal apex, typical and observed*.—Acute.
*Sepal base, typical and observed*.—Acute.
*Sepal margin, typical and observed*.—Entire.
*Sepal surface, typical and observed*.—Smooth.
*Sepal color, abaxial and adaxial typical and observed*.—146 C.
*Peduncle length, typical and observed*.—17 mm.
*Peduncle diameter, typical and observed*.—2 mm.
*Peduncle color, typical and observed*.—Close to 145 C.
*Peduncle surface, typical and observed*.—Glossy.
*Carpel color*.—146 B.
*Carpel surfaces*.—Glabrous.
*Stigma*.—Shape — triangular, size — 1 mm, Color 146 C.
*Style*.—Length — 2 mm, shape — slender, Color 146 C.
*Ovary*.—Size — 1 mm long, shape — cordate, Color 146 C.
*Stamens*.—Less than 1 mm across, 2 mm long, quantity — 60, Anthers 60.
*Anthers*.—Dorsifixed and narrow oblong in shape, color — 21 B.
*Pollen color*.—Close to 21 B.
*Scent*.—No scent noticed.
*Fertility*.—None observed.
*Fruit*.—Brown, 3 mm across, 4 mm tall. Seed — none observed.
*Hardiness*.—U.S.D.A. hardiness zones 5-10.
*Disease resistance*.—Resistance to diseases common to *Delosperma* has not been observed on plants grown under nursery conditions.
*Pest resistance*.—Resistance to pests common to *Delosperma* has not been observed on plants grown under nursery conditions.

I claim:

1. A new, distinct *Delosperma* plant as illustrated and described, characterized by orange and pink flowers, compared to the red and orange of the parent plant.

* * * * *